(12) United States Patent
Bettuchi et al.

(10) Patent No.: US 8,740,925 B2
(45) Date of Patent: Jun. 3, 2014

(54) TROCAR ASSEMBLY

(75) Inventors: Michael Bettuchi, Middletown, CT (US); Robert C. Smith, Middletown, CT (US); Michael Davis, Middletown, CT (US); Brian Rockrohr, Waterbury, CT (US); Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 397 days.

(21) Appl. No.: 12/573,283

(22) Filed: Oct. 5, 2009

(65) Prior Publication Data

US 2010/0094228 A1 Apr. 15, 2010

Related U.S. Application Data

(60) Provisional application No. 61/104,433, filed on Oct. 10, 2008.

(51) Int. Cl.
*A61B 17/34* (2006.01)
*A61M 5/178* (2006.01)

(52) U.S. Cl.
USPC ..................... 606/185; 604/170.02

(58) Field of Classification Search
USPC ............ 604/167.03–167.06, 170.02, 166.01, 604/264; 606/185, 167; 600/114, 117, 104, 600/129, 160, 137, 138, 165, 176
See application file for complete search history.

(56) References Cited

U.S. PATENT DOCUMENTS

| | | | |
|---|---|---|---|
| 4,917,112 A * | 4/1990 | Kalt | 602/58 |
| 5,308,336 A | 5/1994 | Hart et al. | |
| 5,628,732 A | 5/1997 | Antoon, Jr. et al. | |
| 5,704,914 A | 1/1998 | Stocking et al. | |
| 5,741,228 A | 4/1998 | Lambrecht et al. | |
| 5,788,676 A | 8/1998 | Yoon | |
| 5,792,113 A | 8/1998 | Kramer et al. | |
| 5,797,888 A | 8/1998 | Yoon | |
| 5,814,026 A | 9/1998 | Yoon | |
| 5,820,600 A | 10/1998 | Carlson et al. | |
| 5,840,063 A | 11/1998 | Flaherty | |
| 5,913,847 A | 6/1999 | Yoon | |
| 5,921,264 A | 7/1999 | Paradis | |

(Continued)

FOREIGN PATENT DOCUMENTS

| | | |
|---|---|---|
| EP | 2 016 972 A2 | 1/2009 |
| WO | WO 99/52577 A1 | 10/1999 |

OTHER PUBLICATIONS

European Search Report for EP 09252393.5-1269 date of completion is Feb. 26, 2010 (4 pages).

*Primary Examiner* — Nicholas Lucchesi
*Assistant Examiner* — Pritesh Patel

(57) ABSTRACT

A surgical system comprising a cannula assembly and an obturator assembly for penetrating tissue is disclosed. A cover of the cannula assembly is mounted to a cannula housing and has a cover aperture therethrough. The cover has a trailing end face defining a predetermined geometrical configuration, at least a portion of the trailing end face is obliquely arranged relative to a longitudinal axis and terminates in, and leads toward the cover aperture to facilitate guiding of the surgical object through the cover aperture. The obturator assembly includes an obturator housing and an obturator member. The obturator housing has a housing base defining a leading end face, which defines a predetermined geometrical configuration corresponding to the predetermined geometrical configuration of the trailing end face of the cover to mate therewith upon assembly of the obturator assembly with the cannula assembly.

17 Claims, 19 Drawing Sheets

(56) References Cited

U.S. PATENT DOCUMENTS

| | | |
|---|---|---|
| 5,947,930 A | 9/1999 | Schwemberger et al. |
| 5,989,232 A | 11/1999 | Yoon |
| 5,989,233 A | 11/1999 | Yoon |
| 6,066,117 A | 5/2000 | Fox et al. |
| D426,635 S | 6/2000 | Haberland et al. |
| 6,083,203 A | 7/2000 | Yoon |
| 6,187,347 B1 * | 2/2001 | Patterson et al. ............. 424/646 |
| D443,360 S | 6/2001 | Haberland |
| 6,258,065 B1 | 7/2001 | Dennis et al. |
| D449,887 S | 10/2001 | Haberland et al. |
| 6,319,266 B1 | 11/2001 | Stellon et al. |
| 6,482,181 B1 | 11/2002 | Racenet et al. |
| 6,551,282 B1 | 4/2003 | Exline et al. |
| 6,595,946 B1 | 7/2003 | Pasqualucci |
| 6,702,787 B2 | 3/2004 | Racenet et al. |
| 6,755,825 B2 | 6/2004 | Shoenman et al. |
| 6,860,869 B2 | 3/2005 | Dennis |
| 6,923,783 B2 | 8/2005 | Pasqualucci |
| 6,942,671 B1 | 9/2005 | Smith |
| 7,011,314 B2 | 3/2006 | McFarlane |
| 7,025,747 B2 | 4/2006 | Smith |
| 7,083,626 B2 | 8/2006 | Hart et al. |
| 7,153,319 B1 | 12/2006 | Haberland et al. |
| 7,163,525 B2 | 1/2007 | Franer |
| 7,169,130 B2 | 1/2007 | Exline et al. |
| 7,217,277 B2 | 5/2007 | Parihar et al. |
| 7,232,004 B2 | 6/2007 | Bartel |
| 7,244,244 B2 | 7/2007 | Racenet et al. |
| 7,300,399 B2 | 11/2007 | Bonadio et al. |
| 7,311,706 B2 | 12/2007 | Schoenman et al. |
| 7,371,227 B2 | 5/2008 | Zeiner |
| 7,390,317 B2 | 6/2008 | Taylor et al. |
| 7,438,702 B2 | 10/2008 | Hart et al. |
| 7,473,243 B2 | 1/2009 | Dennis et al. |
| 7,481,795 B2 | 1/2009 | Thompson et al. |
| 7,540,839 B2 | 6/2009 | Butler et al. |
| 7,559,893 B2 | 7/2009 | Bonadio et al. |
| 7,559,918 B2 | 7/2009 | Pasqualucci |
| 7,563,250 B2 | 7/2009 | Wenchell |
| 7,585,288 B2 | 9/2009 | Haberland et al. |
| 7,591,802 B2 | 9/2009 | Johnson et al. |
| 7,597,701 B2 | 10/2009 | Hueil et al. |
| 7,608,082 B2 | 10/2009 | Cuevas et al. |
| 2004/0260244 A1 | 12/2004 | Piechowicz et al. |
| 2005/0070850 A1 | 3/2005 | Albrecht |
| 2005/0212221 A1 * | 9/2005 | Smith et al. .................... 277/628 |
| 2006/0253077 A1 | 11/2006 | Smith |
| 2007/0225652 A1 * | 9/2007 | Scherr ............................ 604/180 |
| 2008/0009894 A1 * | 1/2008 | Smith ............................ 606/185 |
| 2008/0014251 A1 * | 1/2008 | Benz et al. .................... 424/445 |

* cited by examiner

TROCAR ASSEMBLY

CROSS-REFERENCE TO RELATED APPLICATIONS

The present application claims the benefit of and priority to U.S. Provisional Patent Application Ser. No. 61/104,433 filed on Oct. 10, 2008, the entire contents of which being herein incorporated by reference in its entirety.

BACKGROUND

1. Technical Field

The present disclosure relates to a trocar assembly for use in minimally invasive surgical procedures including endoscopic, laparoscopic and arthroscopic type procedures.

2. Discussion of Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. One example of a safety shield mechanism is disclosed in commonly assigned U.S. Pat. No. 6,319,266 to Stellon et al., the entire contents of which are hereby incorporated by reference.

SUMMARY

Accordingly, the present disclosure is directed to a surgical system for penetrating tissue. The surgical system for penetrating tissue includes a cannula assembly and an obturator assembly at least partially positionable within the cannula assembly. The cannula assembly includes a cannula housing having a cannula sleeve depending from the cannula housing, an object seal disposed relative to the cannula housing and being adapted to establish a substantial seal about an object inserted therethrough and a cover mounted to the cannula housing and having a cover aperture therethrough. The cover has a trailing end face defining a predetermined geometrical configuration. At least a portion of the trailing end face is obliquely arranged relative to the longitudinal axis and terminates in, and leads toward, the cover aperture to facilitate guiding of the surgical object through the cover aperture. The obturator assembly includes an obturator housing having a housing base defining a leading end face. The leading end face defines a predetermined geometrical configuration corresponding to the predetermined geometrical configuration of the trailing end face of the cover to mate therewith upon assembly of the obturator assembly with the cannula assembly. An obturator member extends from the obturator housing and has a leading penetrating member adapted to penetrate tissue. The obturator assembly includes an obturator sleeve dimensioned to at least partially accommodate the obturator member. The obturator sleeve is adapted for longitudinal movement from an advanced position to a retracted position relative to the obturator member.

In disclosed embodiments, the obturator assembly includes an obturator sleeve, the obturator sleeve dimensioned to at least partially accommodate the obturator member.

In disclosed embodiments, the obturator sleeve is adapted for longitudinal movement from an advanced position to a retracted position relative to the obturator member.

In disclosed embodiments, the surgical system includes a zero closure disposed in mechanical cooperation with the cannula housing, the zero closure valve configured to open to permit passage of a surgical object and thereafter close in the absence of the surgical object.

The present disclosure also relates to an object seal for use with a cannula assembly. The object seal is configured to maintain a substantially fluid-tight seal with respect to an object inserted therethrough, and comprises a rigid insert and an elastomeric seal. The rigid insert includes a first horizontal surface, a first vertical annular wall disposed inwardly of the first horizontal surface, and a second vertical annular wall disposed inwardly of the first vertical annular wall. The first vertical annular wall having a first diameter, the second vertical annular wall having a second diameter, the first diameter is larger than the second diameter. The elastomeric seal is disposed in mechanical cooperation with the rigid insert and including a horizontal surface disposed within the second vertical annular wall. The elastomeric seal includes an aperture disposed therein for accommodating insertion of a surgical instrument therethrough. The aperture defines a third diameter which is smaller than the second diameter.

In disclosed embodiments, the elastomeric seal is overmolded onto the rigid insert.

In disclosed embodiments, the rigid insert is made of plastic.

In disclosed embodiments, the rigid insert comprises a distally-depending lip, the lip being configured to engage a portion of a cannula housing.

The present disclosure also relates to a surgical system for penetrating tissue, which comprises a cannula assembly and an obturator assembly. The cannula assembly includes a cannula housing, a cannula sleeve and an object seal. The object seal includes a rigid insert and an elastomeric seal. The rigid insert includes a first horizontal surface, a first vertical wall disposed inwardly of the first horizontal surface, and a second vertical wall disposed inwardly of the first vertical wall. The first vertical wall has a first diameter, and the second vertical wall has a second diameter. The first diameter is larger than the second diameter. The elastomeric seal is disposed in mechanical cooperation with the rigid insert and includes a horizontal surface disposed within the second vertical annular wall, and an aperture for accommodating insertion of a surgical instrument therethrough. The aperture defines a third diameter which is smaller than the second diameter. The obturator assembly is at least partially positionable within the cannula assembly. The obturator assembly includes an obturator housing and an obturator member extending from the obturator housing and having a leading penetrating member adapted to penetrate tissue.

In disclosed embodiments, the obturator assembly includes an obturator sleeve, the obturator sleeve dimensioned to at least partially accommodate the obturator member.

In disclosed embodiments, the obturator sleeve is adapted for longitudinal movement from an advanced position to a retracted position relative to the obturator member.

In disclosed embodiments, the elastomeric seal is overmolded onto the rigid insert.

In disclosed embodiments, the rigid insert is made of plastic.

In disclosed embodiments, the rigid insert comprises a distally-depending lip, the lip being configured to engage a portion of a cannula housing.

In disclosed embodiments, the surgical system includes a zero closure disposed in mechanical cooperation with the cannula housing, the zero closure valve configured to open to permit passage of a surgical object and thereafter close in the absence of the surgical object.

BRIEF DESCRIPTION OF THE DRAWINGS

Various embodiments of the present disclosure are described hereinbelow with references to the drawings, wherein.

DETAILED DESCRIPTION

Figure 1:
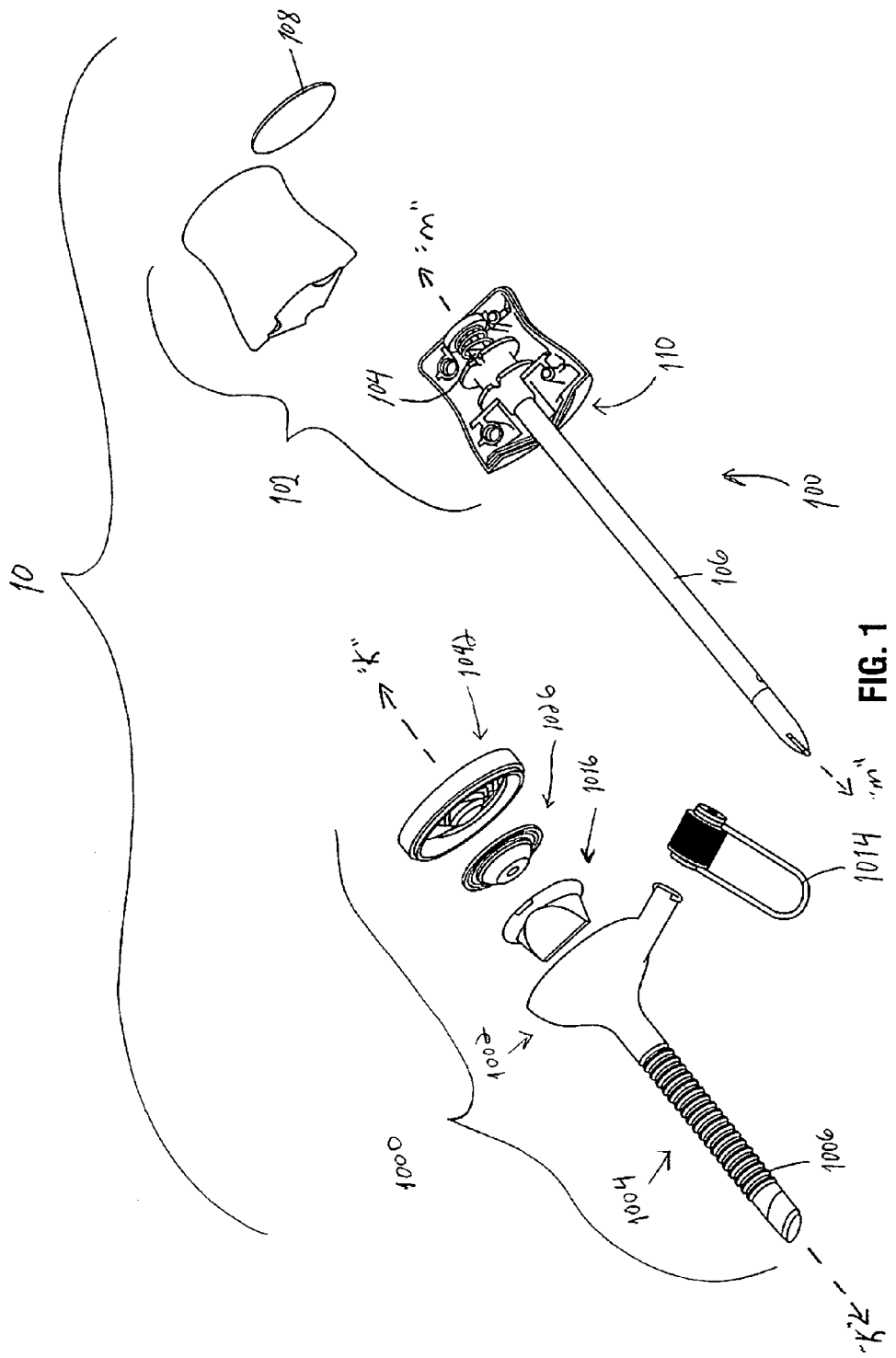
FIGS. 1-21 illustrate various components of the trocar assembly in accordance with embodiments of the present disclosure.

Referring now in detail to the drawing figures, in which, like references numerals identify similar or identical elements, there is illustrated, in FIG. 1, a trocar assembly constructed in accordance with various embodiments of the present disclosure and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000. Trocar assembly 10 may have various dimensions or diameters. In one embodiment, trocar assembly 10 provides a 5 mm portal to an underlying tissue or target site.

Figure 2:
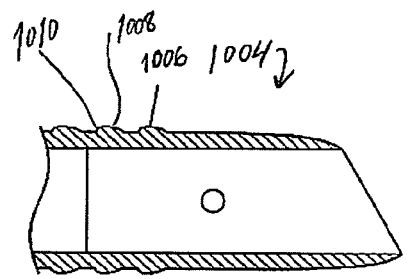
Figure 3:
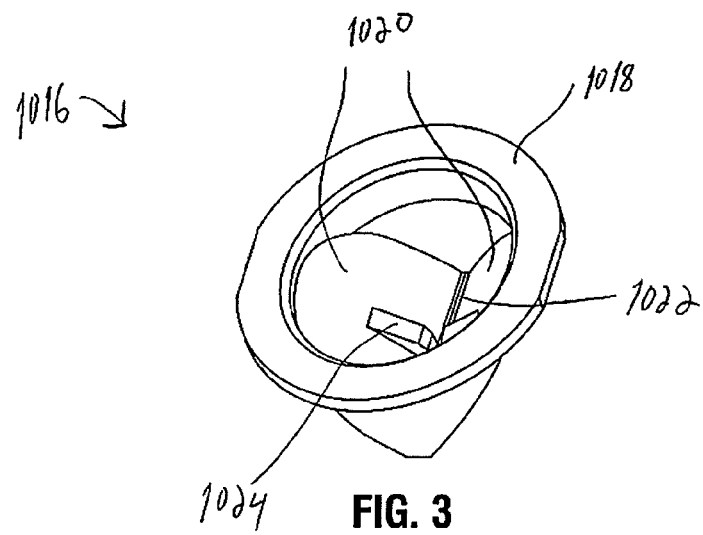
Figure 4:
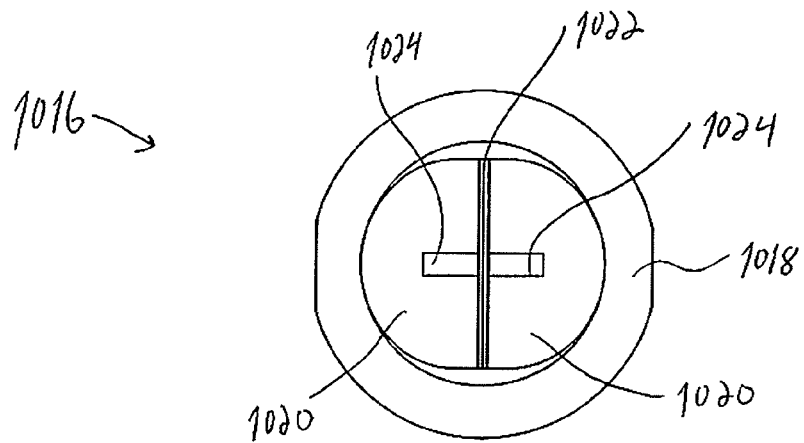
Figure 5:
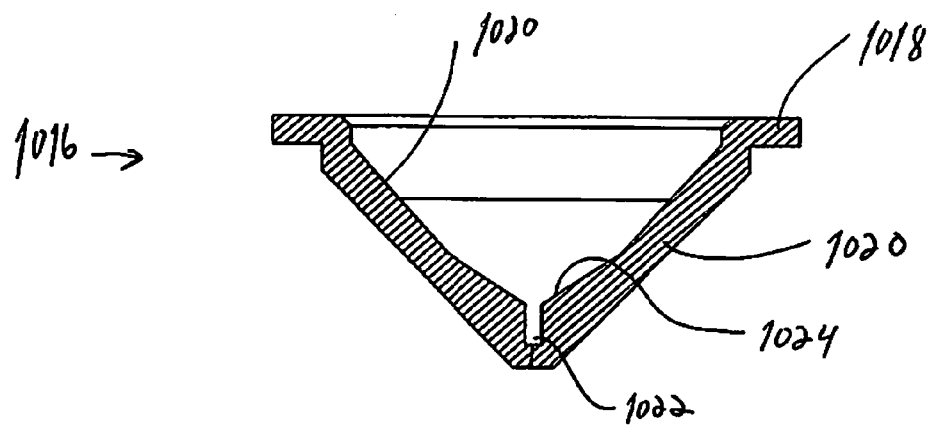
Figure 6:
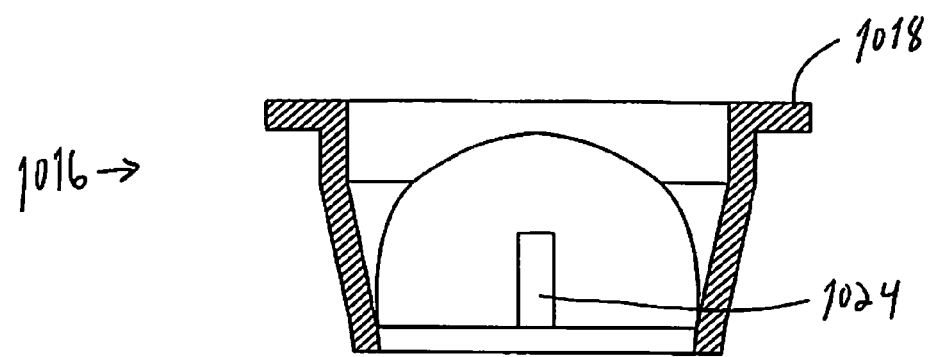
Figure 7:
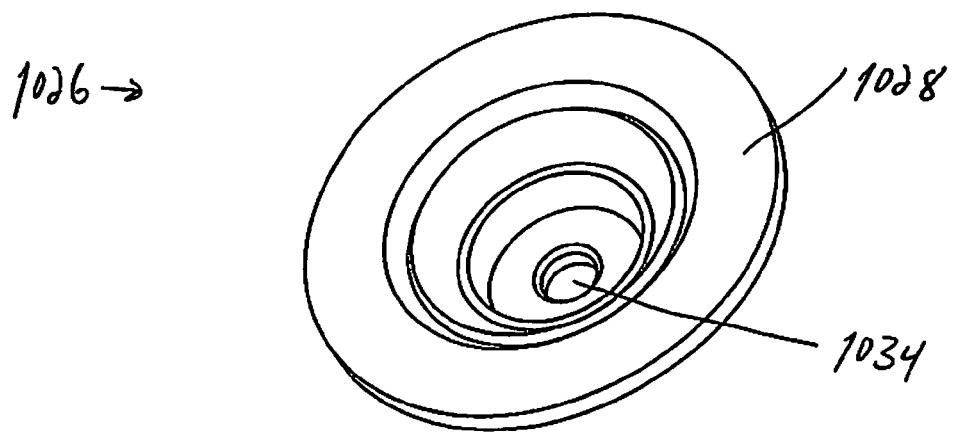
Figure 8:
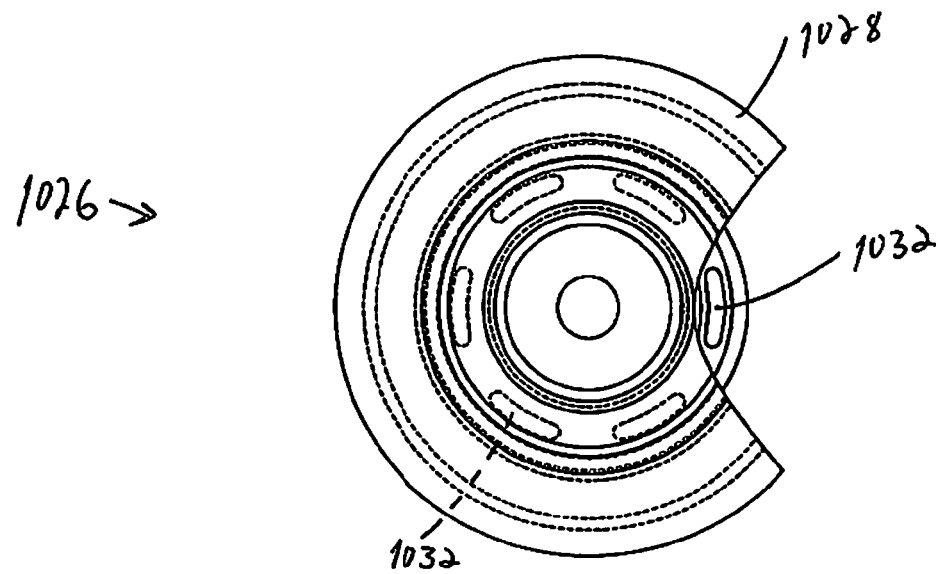
Figure 9:
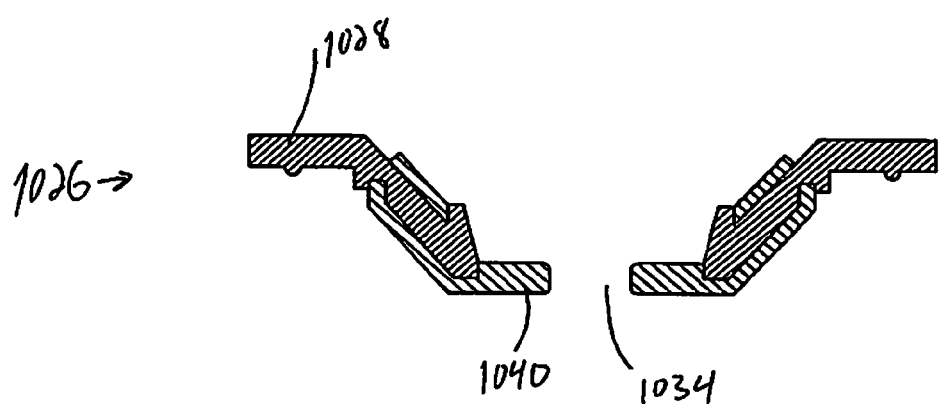
Figure 10:
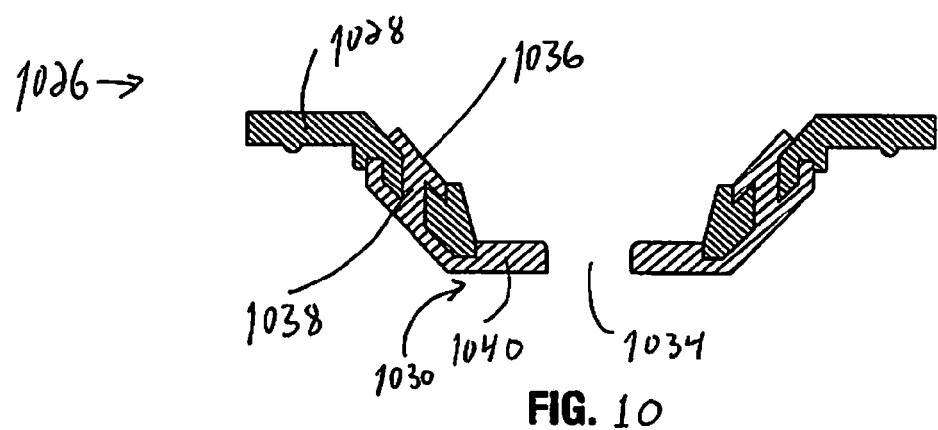

Cannula assembly 1000 may be suitable for use in any endoscopic procedures including, e.g., laparoscopic and arthroscopic. In disclosed embodiments, cannula assembly 1000 includes cannula housing 1002 and cannula sleeve 1004 extending from the cannula housing 1002. Either or both cannula housing 1002 and cannula sleeve 1004 may be transparent in part or in whole and may be fabricated from biocompatible metal or polymeric material. Cannula 1004 may include a plurality of spaced locking ribs or projections 1006 extending about the periphery of the sleeve (FIGS. 1-2). Ribs 1006 may be generally annular in configuration and may be spaced along longitudinal axis "k". Ribs 1006 may further define a tapered leading surface 1008 and a trailing locking surface 1010 traversing the longitudinal axis "k". Tapered leading surface 1008 facilitates insertion of a cannula sleeve 1004 within the tissue. Trailing locking surfaces 1010 are dimensioned to engage the tissue substantially preventing or minimizing retropulsion of cannula sleeve 1004 relative to the tissue. Cannula housing 1002 may include port extension 1012 depending from base of the housing 1002. Port extension 1012 is in fluid communication with the internal passageway of cannula sleeve 1004. Port extension 1012 may have luer connector 1014 releasably connected thereto, or permanently affixed to cannula housing 1002. Luer connector 1014 may be adapted for connection to a source of insufflation gases or another fluid source such as, e.g., an irrigant fluid used in an arthroscopic procedure.

Cannula housing 1002 further includes zero closure valve 1016. (FIGS. 1 and 3-6). Zero closure valve 1016 is adapted to open to permit passage of the surgical object and thereafter close in the absence of the object. Zero closure valve 1016 includes outer flange 1018 and inner valve surfaces 1020 depending radially inwardly from the outer flange 1018. Inner seal surfaces 1020 may extend in both a radial and longitudinal direction and terminate at slit 1022. A pair of opposed rails 1024 are disposed on the leading end face of zero closure valve 1016. Rails 1024 provide additional rigidity or support to inner valve surfaces 1020 to facilitate closing of the valve 1016 and/or minimize damage to valve 1016 during insertion of a relatively sharp object. Other zero closure valves such as duck bill valves are also envisioned.

With reference to FIGS. 1 and 7-10, cannula housing further includes object seal 1026. Object seal 1026 may be substantially similar to the seal disclosed in commonly assigned U.S. patent application Ser. No. 11/406,992, filed Apr. 19, 2006, the entire contents of such disclosure being herby incorporated by reference herein. Object seal 1026 includes annular seal mount 1028 and resilient seal 1030 connected to the mount 1028. Seal mount 1028 may be formed of a relatively rigid material such as a suitable polymeric material or alternatively may be fabricated from a resilient material. Seal mount 1028 incorporates a plurality of apertures 1032 extending through the wall of the seal mount 1028. Resilient seal 1030 defines aperture 1034 and is arranged to form a substantial seal about an instrument inserted therethrough. In an embodiment, resilient seal 1030 is adapted to form a seal about an instrument having a diameter ranging from about 3 mm to about 7 mm, for example, about 5 mm. In this regard, aperture 1034 of seal 1030 defines a diameter ranging from about 2 mm to about 3 mm. Seal 1030 may be formed of any suitable elastomeric material. In disclosed embodiments, seal 1030 is integrally formed with seal mount 1028 such that the elastomeric material communicates through apertures 1032 to form the integrally coupled unit depicted in the drawing sheets. Seal mount 1028 and seal 1030 may be co-molded as is known in the art. In embodiments, seal 1030 is molded with seal mount 1028 to provide annular entry seal portion 1030, anchoring segments or spokes 1038 extending through apertures 1032 of seal mount 1028 and planar inner seal portion 1040. Annular entry seal portion 1030 defines a general frusto-conical configuration. Inner seal portion 1040 defines aperture 1034.

Seal 1030 may include the fabric seal disclosed in commonly-assigned U.S. Pat. No. 6,702,787 to Racenet, the entire contents of which are incorporated herein by reference. The seal disclosed in the Racenet '787 patent may be a septum seal having a first layer of resilient material and at least one fabric layer juxtaposed relative to the first layer. The fabric layer may include a SPANDEX material containing 20% LYCRA from Milliken. Other arrangements for seal 1030 are also envisioned. Seal 1030 may be flat, hemispherical or have any other shape as desired.

Figure 11:
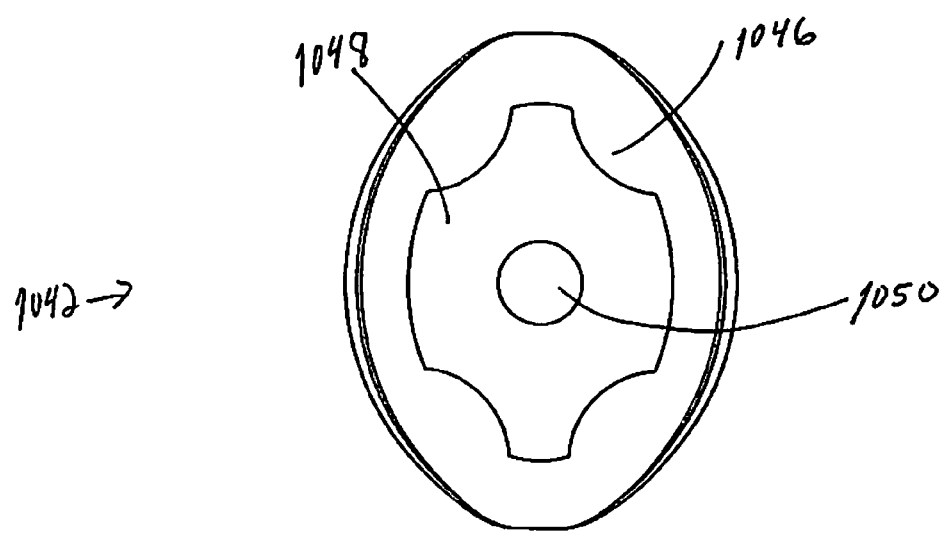
Figure 12:
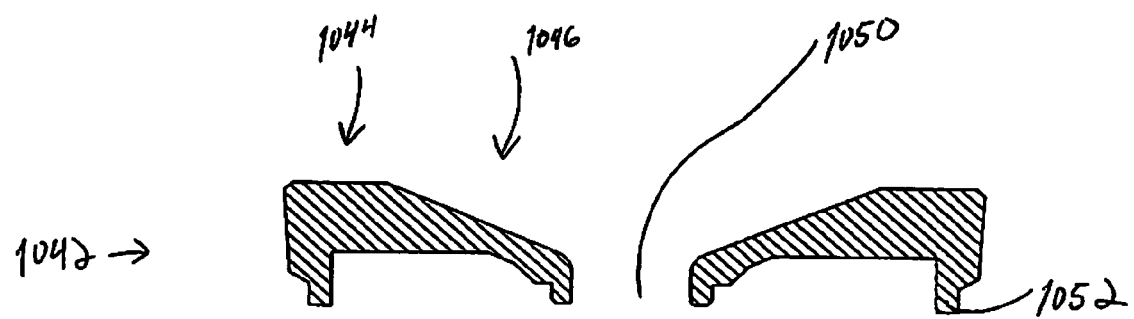

With reference now to FIGS. 1 and 11-12, cannula assembly 1000 further includes cover 1042 which is mounted to cannula housing 1002 to enclose both zero closure valve 1016 and object seal 1026. Cover 1042 may be secured to housing 1002 with the use of adhesives, cements, or via mechanical coupling means such as a segment coupling or snap fit. Cover 1042 includes outer segment 1044 and inner segment 1046 depending radially inwardly from the outer segment 1044.

Cover 1042 may be oblong or elliptical in plan view. The trailing end face of cover 1042 defines a substantial recessed portion or mounting recess 1048 of predetermined geometrical configuration. In embodiments, mounting recess 1048 is generally diamond shaped, key shaped or the particular configuration depicted in the views in FIG. 11. Inner segment 1046 is inclusive of mounting recess 1048 and defines a substantially planar surface obliquely arranged with respect to the longitudinal axis and tapering toward cover aperture 1050. Tapered planar surface 1050 facilitates guiding of a surgical object towards and through cover aperture 1050. Seal cover 1042 further includes peripheral rib 1052 which is received within or over the inner boundary of cannula housing 1002 to facilitate securement to the cannula housing 1002. Ribs 1052 may be dimensioned to frictionally engage the inner boundary of cannula housing 1002.

With reference to FIGS. 1 and 14-21, obturator assembly 100 of trocar assembly 10 will be discussed. Obturator assembly 100 includes obturator housing 102, elongated obturator rod 104 extending distally from the housing 102 and outer sleeve 106 coaxially mounted about the obturator rod 104. In general, outer sleeve 106 is adapted to reciprocate or move in a longitudinal direction between an unarmed and armed condition of obturator rod 104. Obturator rod 104 defines obturator axis "m" and will be discussed in greater detail hereinbelow. Obturator housing 102 includes housing cover or dome 108 mounted thereto. Obturator housing 102 may be two half components connected to each other along respective peripheries thereof. Obturator housing 102 includes leading end 110 which projects outwardly from the obturator housing 102. Leading end 110 is correspondingly dimensioned to be received within mounting recess 1048 of seal cover 1042 in the assembled condition of obturator 100 and cannula housing 1000. For example, leading end 110 may be substantially similar in configuration, e.g., generally key shaped or diamond shaped arrangement, to the configuration of mounting recess 1048 of seal cover 1042. Leading end 110 of obturator housing 102 is generally tapered to facilitate insertion within mounting recess 1048 of seal cover 1042. Thus, in the assembled condition, leading end 110 or face of obturator housing 102 fits or mates with mounting recess 1048 of seal cover 1042. In one embodiment, leading end 110 of obturator housing 102 and mounting recess 1048 of seal cover 1042 establish a mechanical interference or transition fit whereby obturator housing 102 may be readily mounted and dismounted relative to cannula housing 1002. A frictional fit for a more secured condition is also envisioned.

Figure 13:
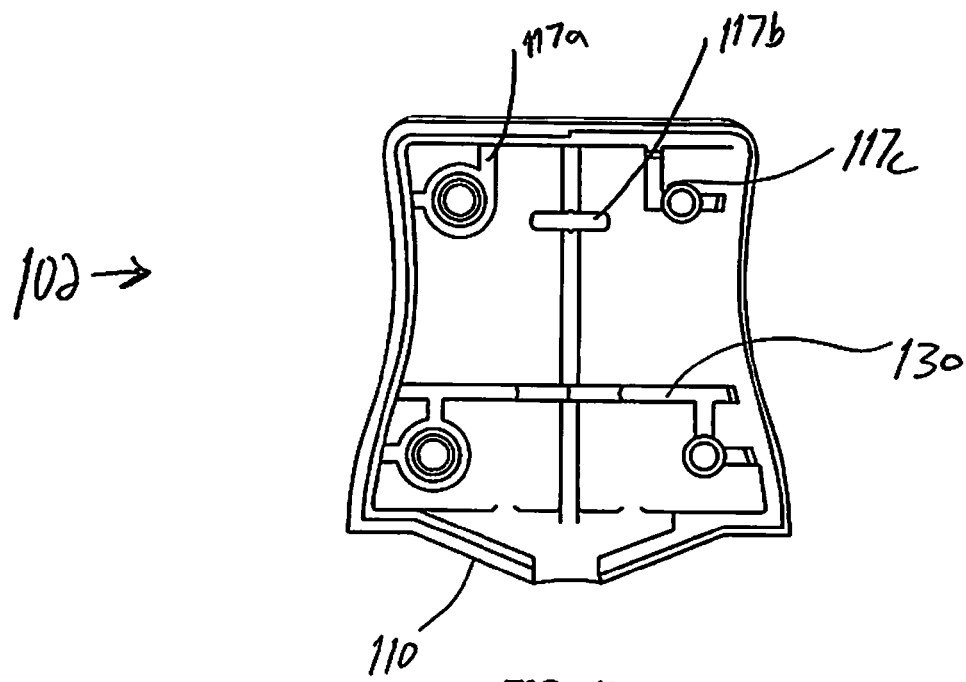
Figure 14:
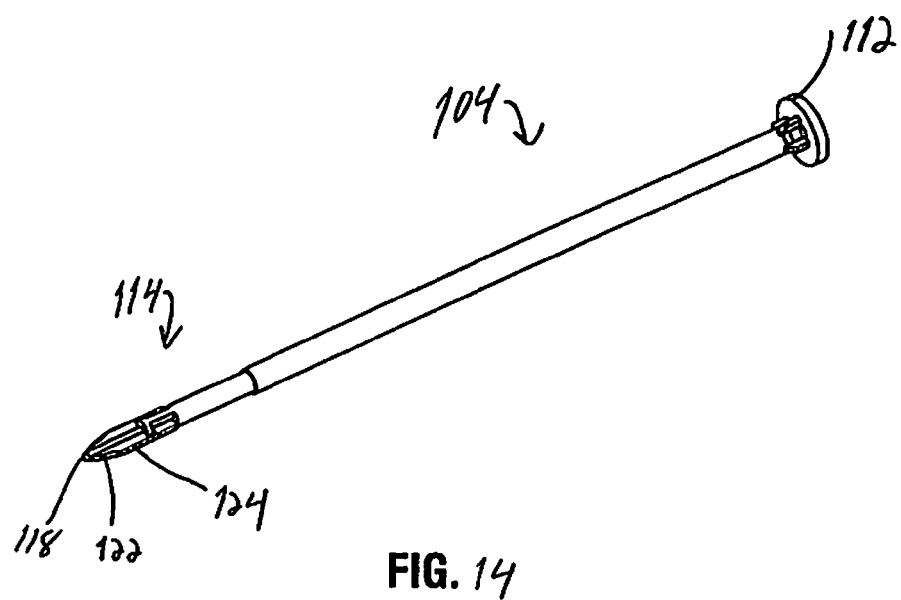
Figure 15:
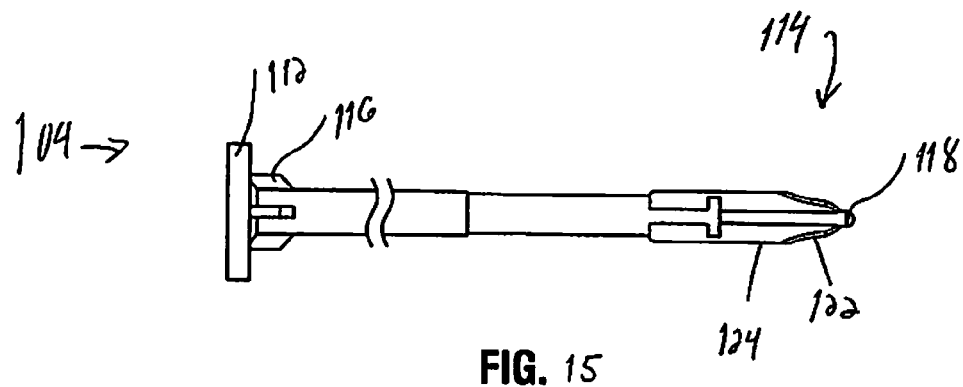
Figure 16:
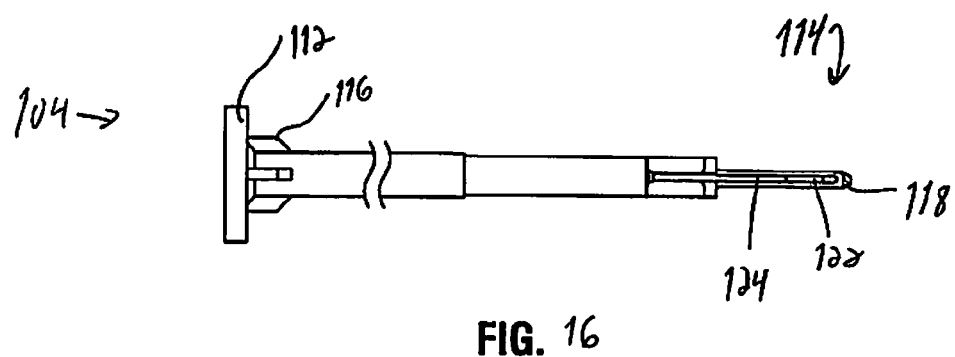
Figure 17:
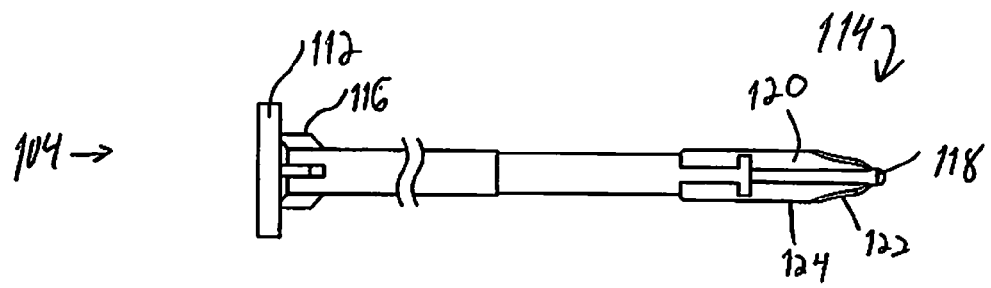
Figure 18:
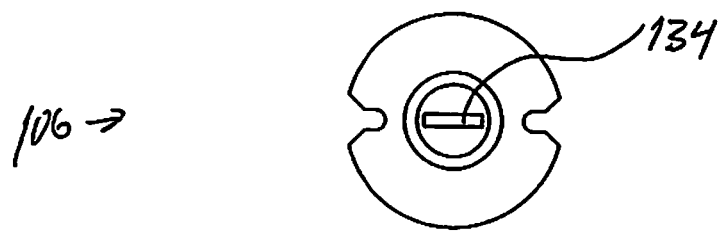
Figure 19:
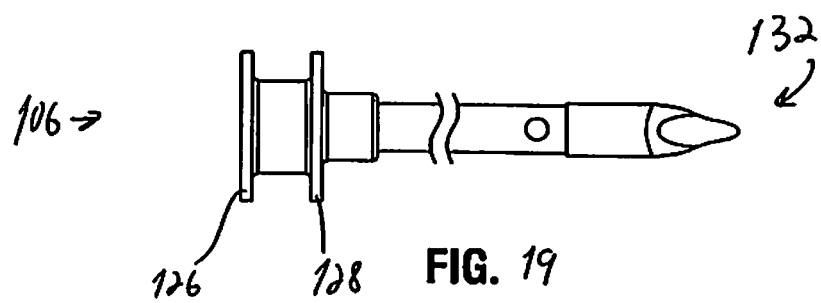
Figure 20:
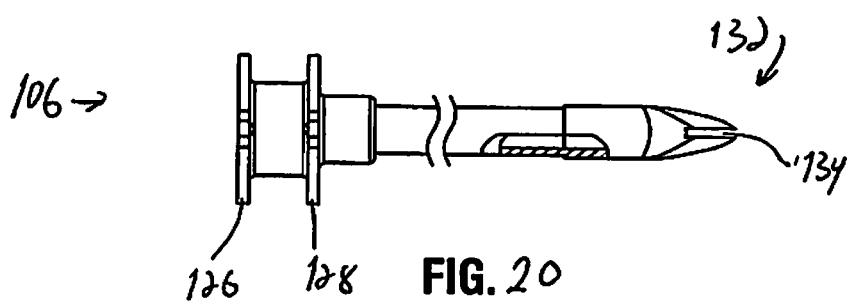
Figure 21:
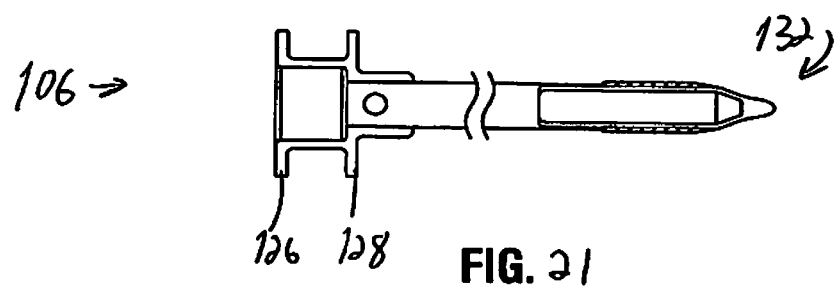

With reference to the FIGS. 1 and 14-17, obturator rod 104 of obturator assembly 100 will be discussed. Obturator rod 104 includes obturator collar 112 at its proximal end, and penetrating head 114 at its distal end. Obturator collar 112 has a plurality of axial ribs 116 extending therefrom along the outer surface of rod 104. Rod 104 may have an outer diameter at its proximal or trailing end which is greater than the outer diameter of the obturator rod. Obturator collar 112 is received within recess defined between walls 117a, 117b, 117c of obturator housing 102 to longitudinally fix the obturator rod 104 relative to obturator housing 102 (FIG. 13). Thus, the aforedescribed mounting arrangement of obturator rod 104 and obturator housing 102 secures the obturator rod 104 from moving in an axial direction relative to obturator housing 102.

Penetrating head 114 may be substantially similar in design to the penetrating member disclosed in commonly assigned U.S. patent application Ser. No. 12/194,629, filed Aug. 20, 2008, the entire contents of which are hereby incorporated by reference. Penetrating head 114 includes cylindrical element 118 and dissecting elements 120 extending contiguously from the cylindrical element 118. Cylindrical element 118 defines an arcuate or rounded leading surface 120 which is atraumatic to tissue and extends a predetermined distance beyond planar dissecting element 120. This consequent narrow profile provided by cylindrical element 118 permits initial insertion within tissue and facilitates, e.g., dissection or advancement, within the tissue without an incising action. Cylindrical element 118 may extend through planar dissecting element 120 to obturator rod 104. Planar dissecting element 120 defines a triangular arrangement having oblique side surfaces 122 leading to parallel end surfaces 124. Side surfaces 122 may be arcuate or rounded as shown to be atraumatic to tissue. In the alternative, side surfaces 122 may be sharpened. End surfaces 124 may be blunt or sharp.

Obturator rod 102 and penetrating head 114 may be integrally, i.e., monolithically formed, as a single unit. In one method, obturator member 104 and head 114 may be formed of a suitable polymeric material through known injection molding techniques. In the alternative, penetrating head 114 and obturator rod 104 may be separate components and connected through a slot and groove arrangement.

As depicted in FIGS. 1 and 18-21, outer sleeve 106 of obturator assembly 100 will be discussed. Outer sleeve 106 is adapted for longitudinal movement relative to obturator rod 104. Outer sleeve 106 includes first and second collars 126, 128 at its proximal end. Collars 126, 128 are longitudinally spaced. Collars 126, 128 reside within collar mounting walls 117b, 130 of obturator housing 102 (FIG. 13) and move within the walls 117b, 130 during traversing movement of outer sleeve 106. Obturator sleeve 106 includes obturator nose 132 at its distal end. Obturator nose 132 may be substantially similar in configuration to the nose 132 described in the aforementioned '629 application. Nose 132 moves relative to penetrating head 114 during longitudinal movement of outer sleeve 106. In the initial or unarmed condition, nose 132 is positioned relative to penetrating head 114 whereby cylindrical element 118 of the penetrating head 114 at least partially extends beyond the nose 132. In addition, side surfaces 122 of planar dissecting element also may extend beyond nose 132, i.e., protrude outwardly from central slot 134. Nose 132 may be generally conical in configuration. Alternatively, nose 132 may also have a slight inward contour along opposed peripheral portions. Various other configurations are also envisioned.

Obturator sleeve 106 may be spring biased in the distal direction by coil spring 134. Coil spring 134 is mounted about obturator rod 102 and engages first collar 126 of obturator sleeve 106.

During use, as obturator sleeve 106 is advanced within tissue, obturator nose 132 engages the tissue causing retraction of the obturator nose 132 and the obturator sleeve 106 against the bias of coil spring 134 to thereby further expose penetrating head 114. Once obturator nose 132 passes through the tissue, obturator sleeve 106 and obturator nose 132 return to its initial position.

Figure 22:
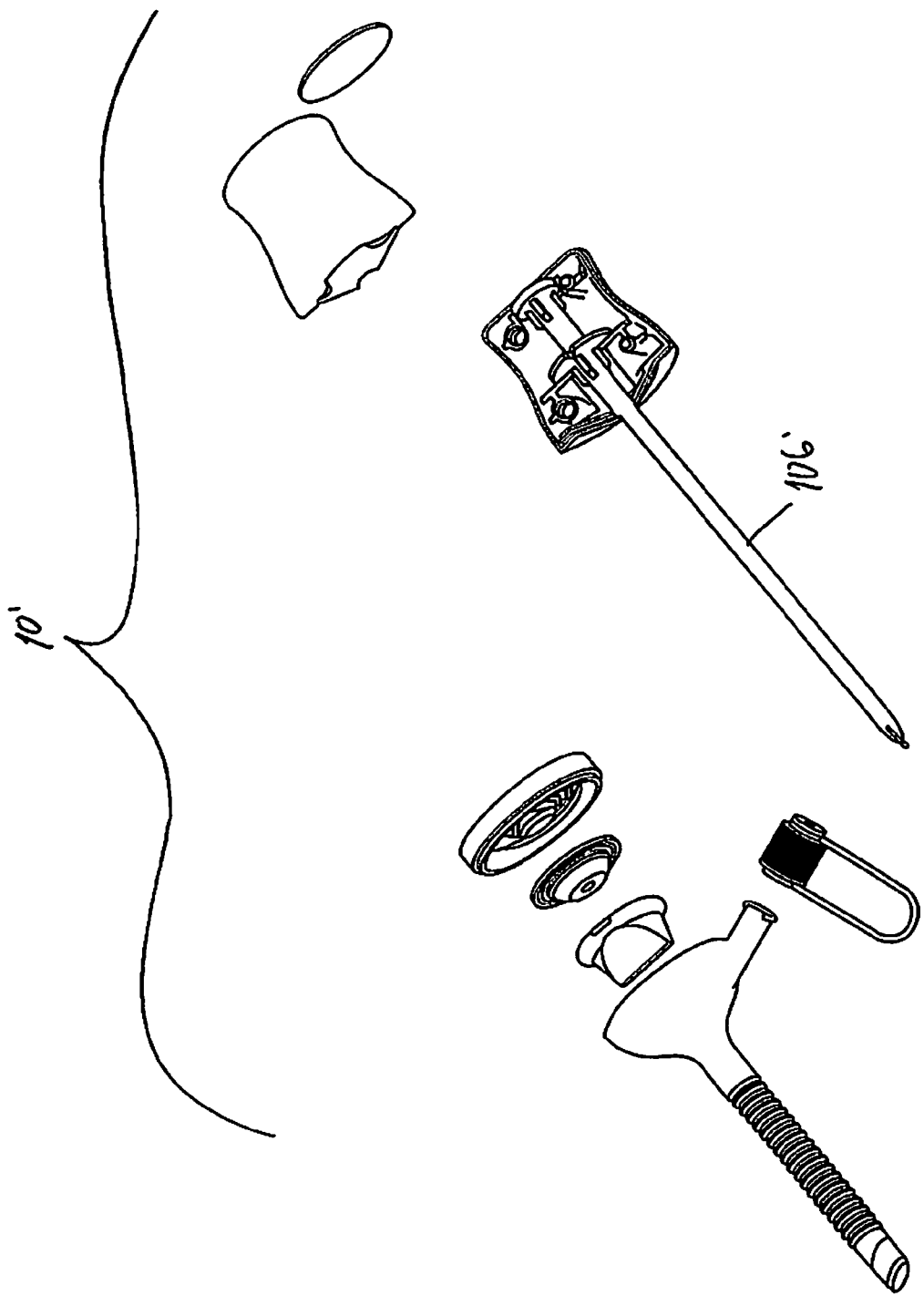
FIGS. 22-23 illustrate various components of another embodiment of a trocar assembly of the present disclosure.
Figure 23:
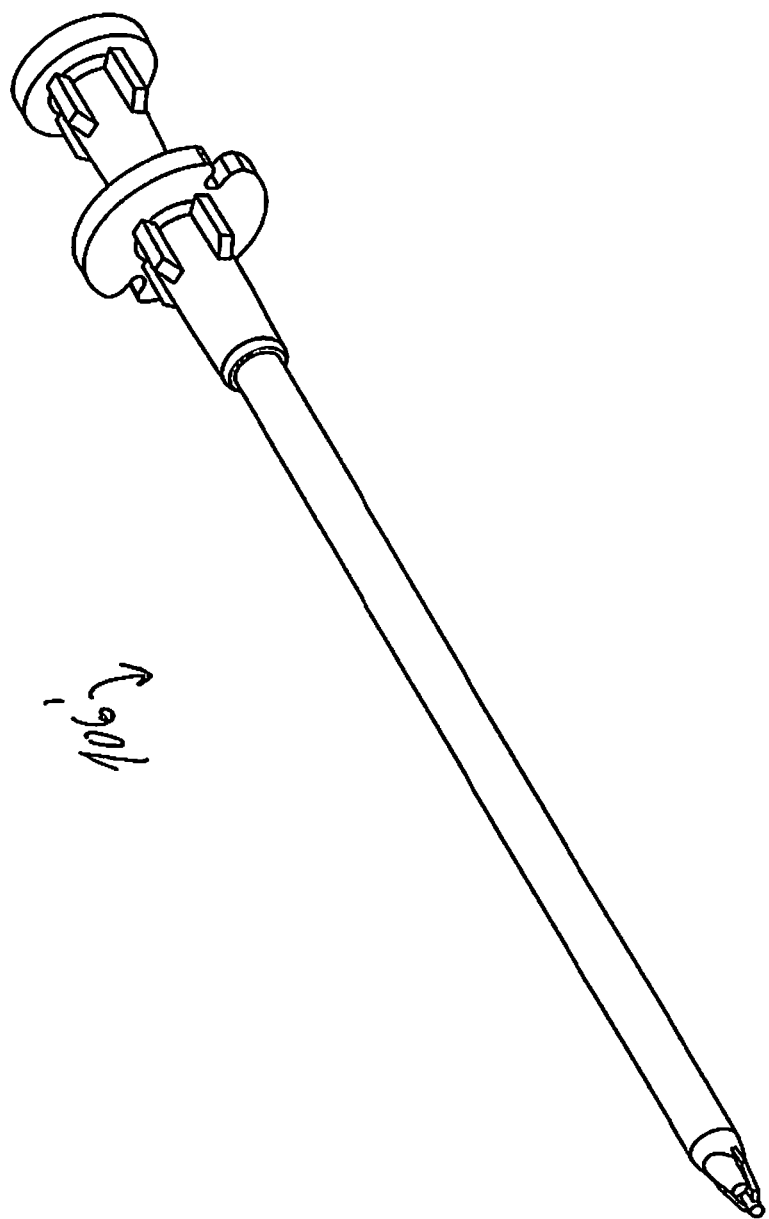

FIGS. 22-23 illustrate another embodiment of the present disclosure. In this embodiment, trocar assembly 10' establishes a 3 mm portal for accessing the underlying tissue site. Most of the components are similar to the aforedescribed embodiment with the exception of a reduction in size. In addition, in accordance with this embodiment, obturator sleeve 106' and obturator rod (from the embodiment illustrated in FIG. 1) are integrally or monolithically formed (FIGS. 22-23). Thus, obturator sleeve 106' will not move in a longitudinal direction relative to the obturator rod. In other regards, this embodiment is substantially similar to the previous embodiment.

FIGS. 24-39 illustrate another embodiment of the present disclosure. With particular reference to FIGS. 24-31, a trocar assembly 2010 (e.g., a 3 mm low profile version) is shown. Trocar assembly 2010 includes an obturator housing 2012 disposed in mechanical cooperation with an elongated obturator member 2014, and defines a longitudinal axis "A-A." The elongated obturator member 2014 extends distally from the obturator housing 2012. The trocar assembly 2010 also includes a cannula assembly 3100 which receives the elongated obturator member 2014.

Figure 25:
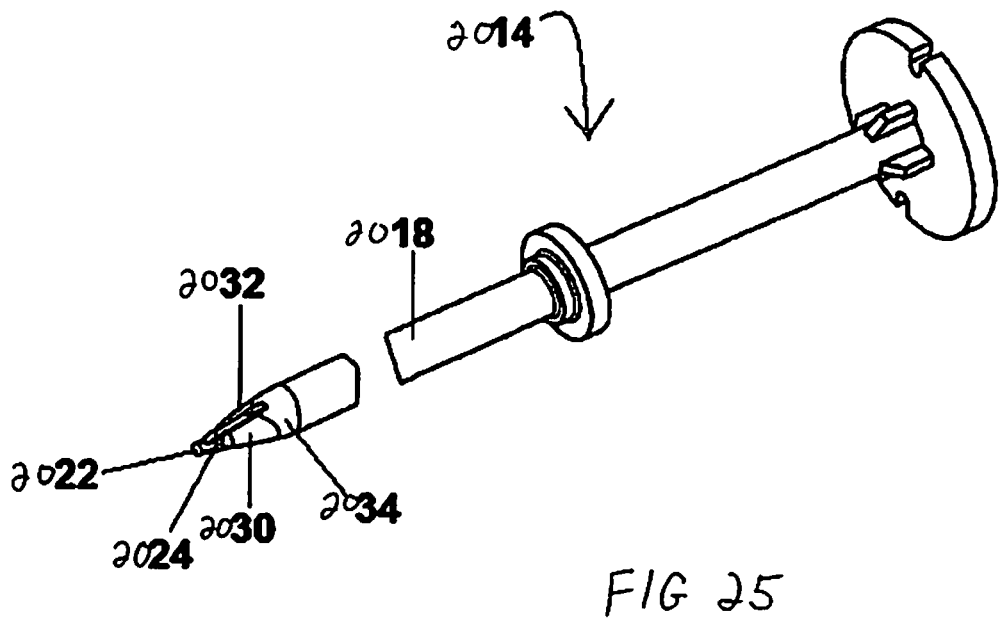
Figure 26:
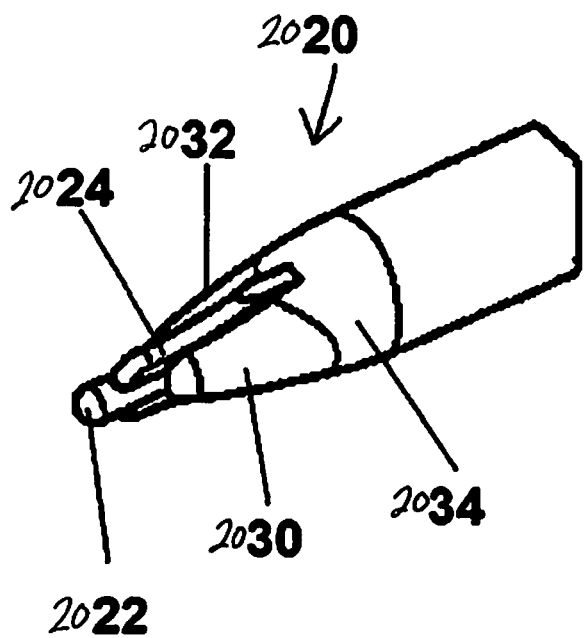

With reference to FIGS. 25 and 26, the obturator member 2014 includes an obturator rod 2018 mechanically engagable with the obturator housing 2012 and a penetrating head 2020 adjacent the distal end of the obturator rod 2018. The penetrating head 2020 includes, from distal to proximal, a cylindrical element 2022 and a dissecting element contiguously extending from the cylindrical element 2022. The cylindrical element 2022 defines a rounded leading surface which is atraumatic to tissue. The cylindrical element 2022 permits initial insertion within an opening in the tissue and facilitates the advancement of the penetrating head 2020 within the tissue. The dissecting element incorporates upper and lower tapered surfaces 2030, 2032 and rounded side surfaces which define a pair of outwardly disposed dissecting fins 2024. The tapered surfaces 2030, 2032 and dissecting fins 2024 are also atraumatic to tissue. The tapered surfaces 2030, 2032 and dissecting fins 2024 further enlarge the opening within the tissue as the penetrating head 2020 is advanced.

Figure 24:
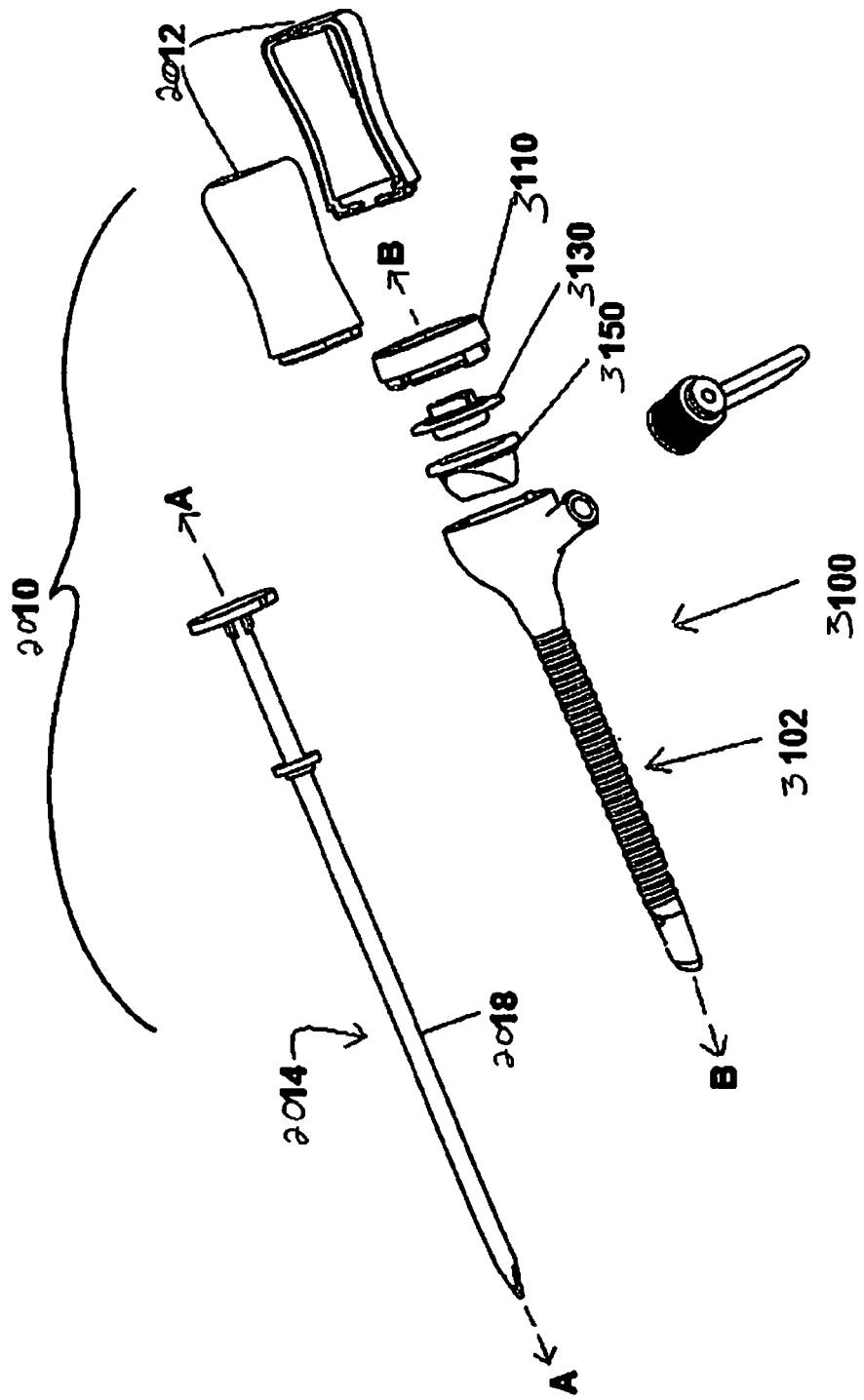
FIGS. 24-31 illustrate various components of another embodiment of a trocar assembly of the present disclosure.
Figure 27:
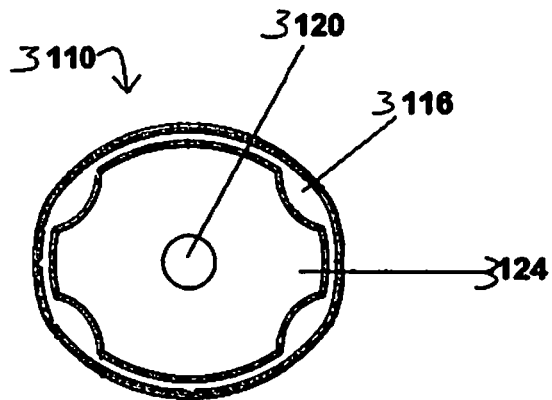
Figure 28:
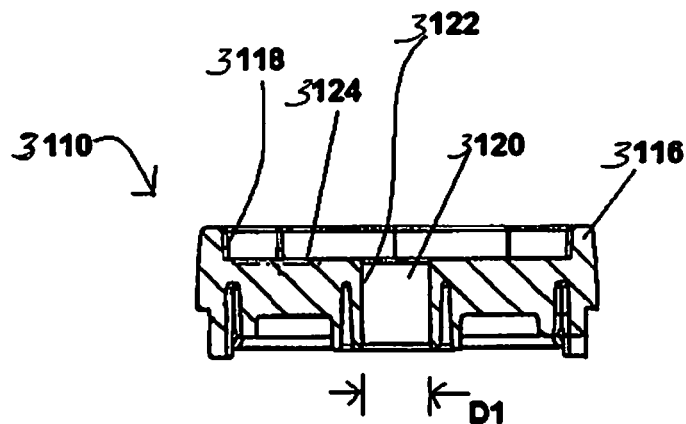
Figure 29:
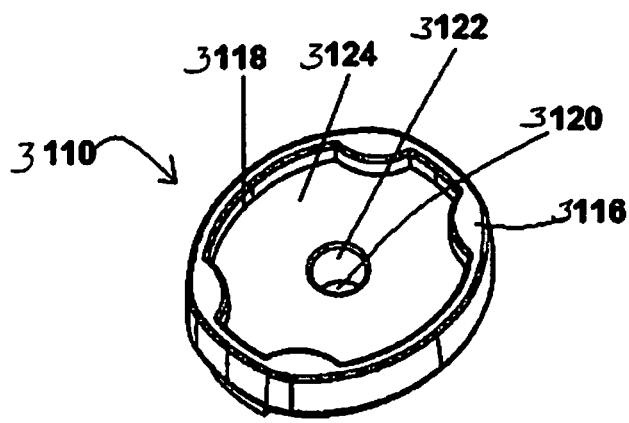
Figure 30:
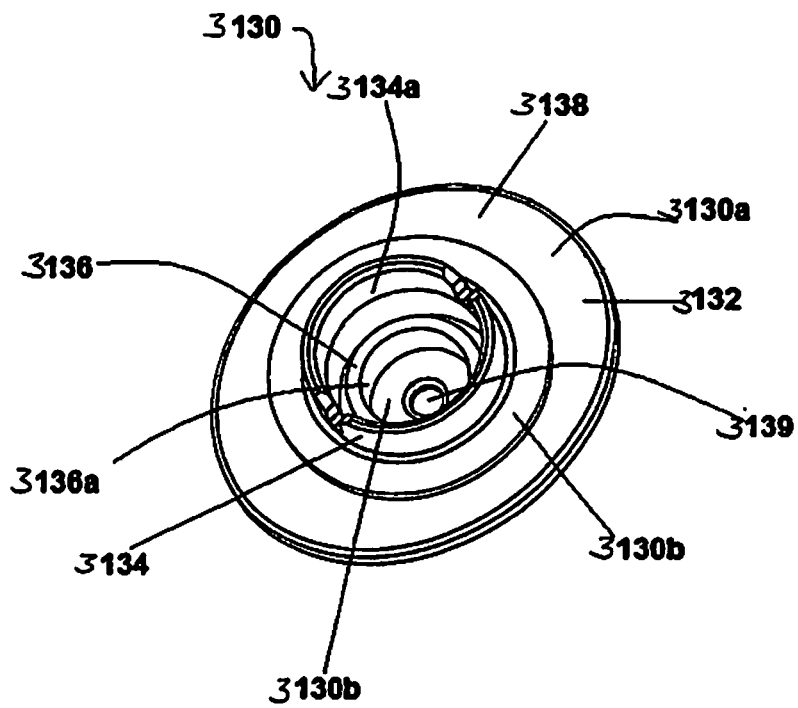
Figure 31:
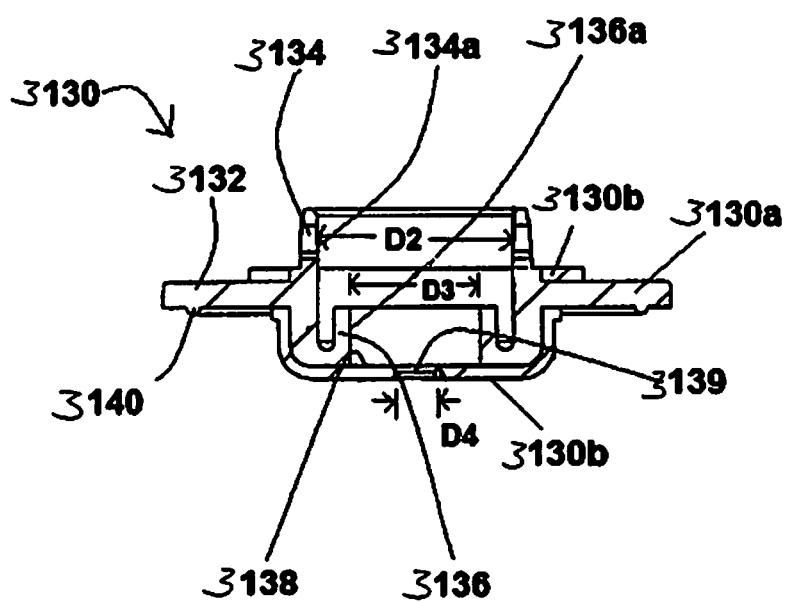
Figure 32:
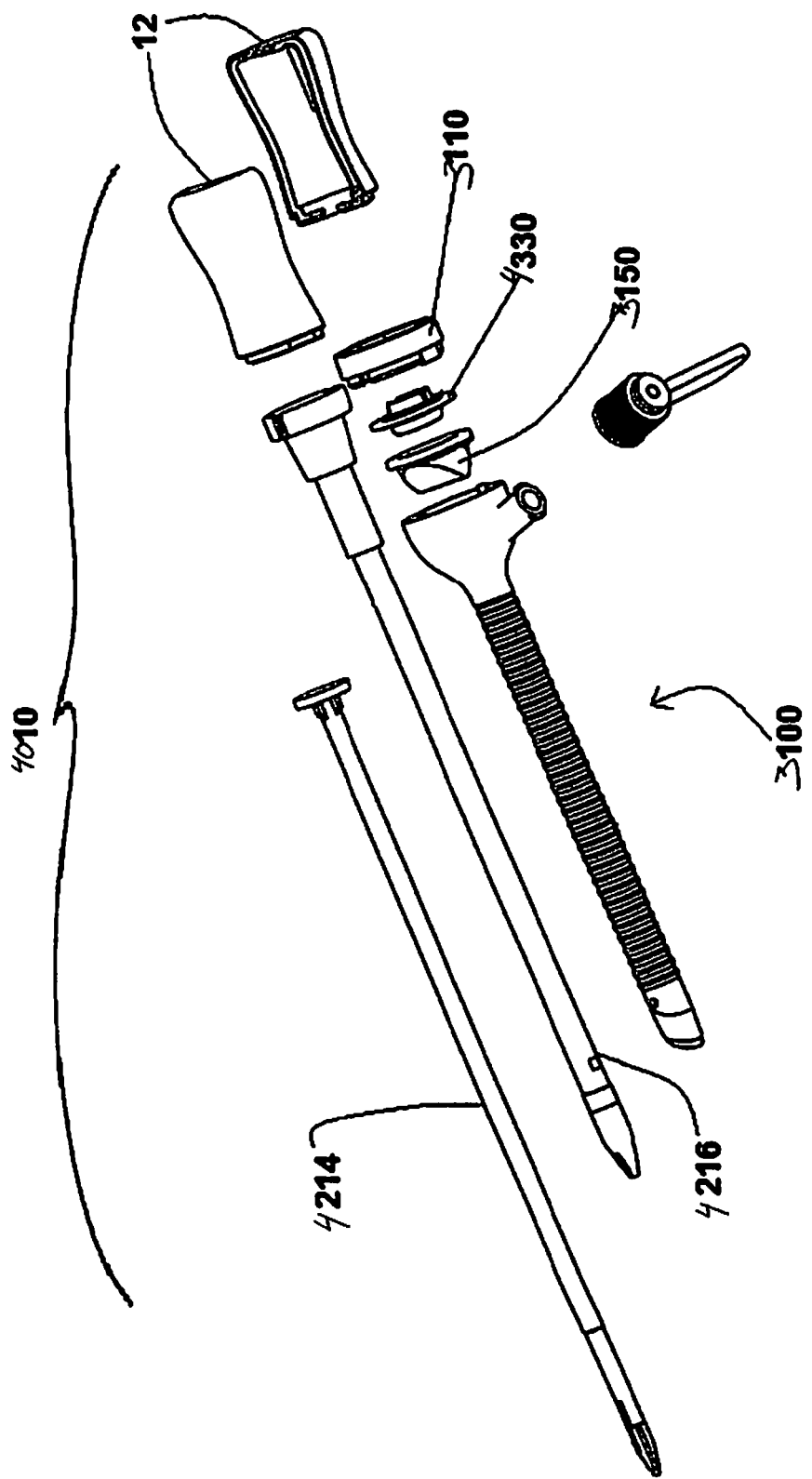
FIGS. 32-39 illustrate various components of another embodiment of a trocar assembly of the present disclosure.
Figure 33:
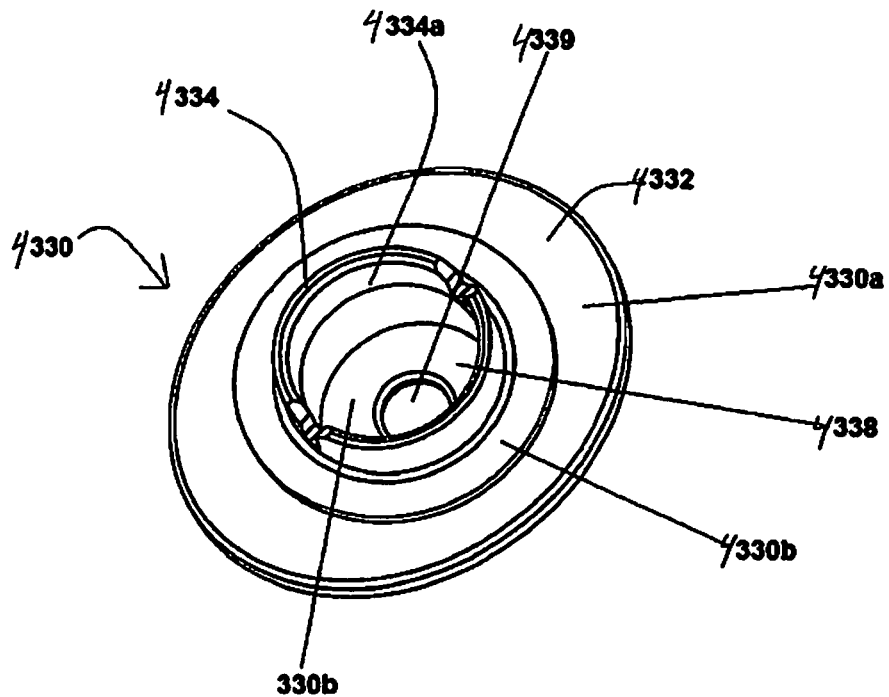
Figure 34:
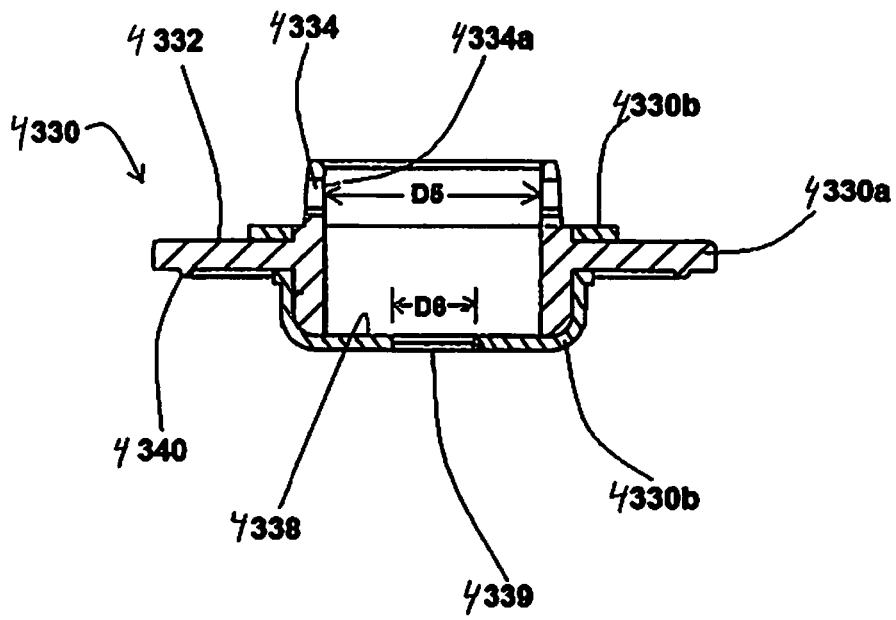
Figure 35:
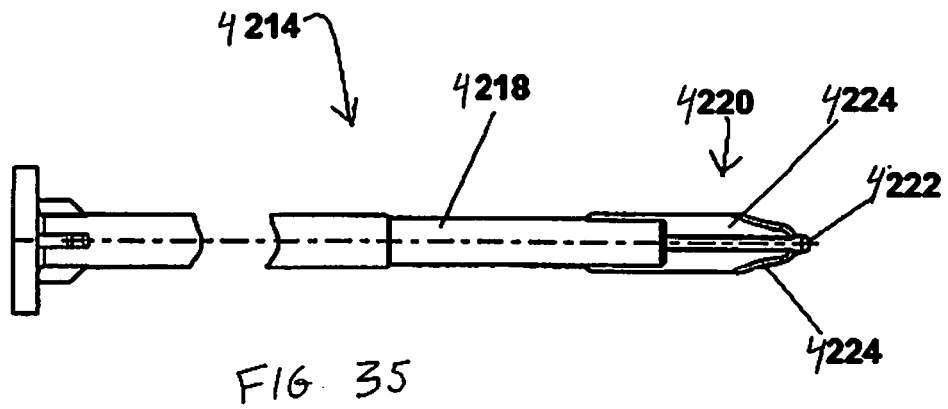
Figure 36:
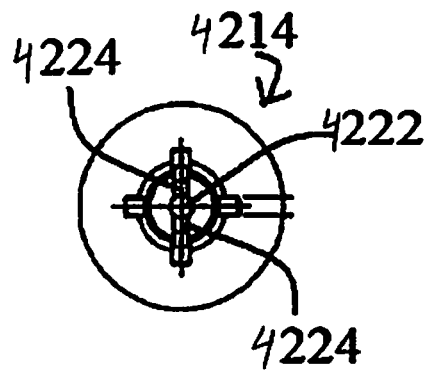
Figure 37:
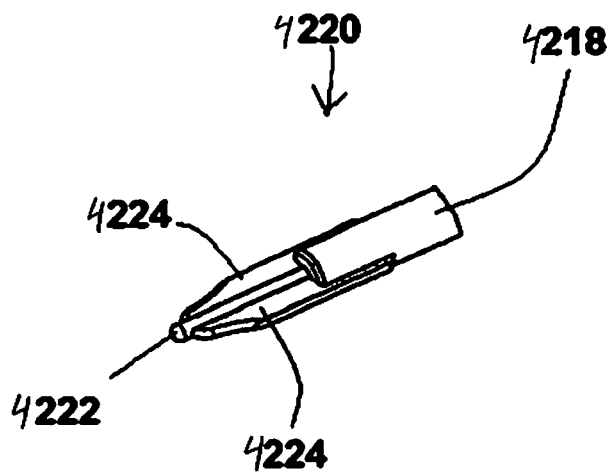
Figure 38:
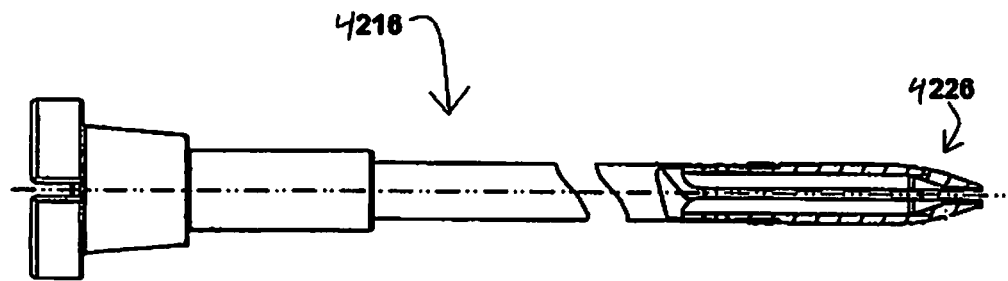
Figure 39:
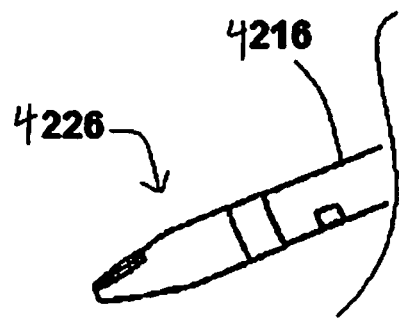

The cannula assembly 3100 of the trocar assembly 2010 includes an elongated portion 3102, defining a longitudinal axis "B-B," and a cover 3110 (FIGS. 27-29). The cover 3110 encloses an object seal 3130 (FIGS. 30-31) and a zero-closure seal 3150 (FIG. 24). The object seal 3130 is disposed proximally of the zero-closure seal 3150. The cover 3110 includes an outer lip 3116 and an aperture 3120 having a diameter of D1. A horizontal shelf 3124 interconnects the outer lip 3116 with the aperture 3120. The outer lip 3116 includes vertical, inner sidewalls 3118. Additionally, the aperture 3120 is defined between vertical, inner sidewalls 3122.

The object seal 3130 includes an elastomeric septum seal 3130b which is over-molded onto a rigid plastic insert 3130a. Rigid plastic insert 3130a includes a horizontal surface 3132, a first vertical, annular wall 3134 and a second vertical, annular wall 3136. An inner vertical surface 3134a of annular wall 3134 defines diameter D2. An inner vertical surface 3136a of annular wall 3136 defines diameter D3. Additionally, the elastomeric septum seal 3130b of the object seal 3130 defines a horizontal surface 3138 disposed within annular wall 3136. The elastomeric septum seal 3130b includes an aperture 3139 having a diameter D4. The diameter D1 of the cover's aperture 3120 is less than the diameter D3 of the annular wall 3136. Thus, upon insertion, the obturator member 2014 is only able to contact the horizontal surface 3138 and the walls defining the aperture 3139 of the object seal 3130.

The object seal 3130 also includes a lip 3140 depending downwardly from horizontal surface 3132. The lip 3140 engages a corresponding detent (not shown) on the housing 3102, such that the object seal 3130 cannot move circumferentially (i.e., about longitudinal axis "B-B") or radially (i.e., transversely with respect to longitudinal axis "B-B"). Additionally, when the cannula assembly 3100 is assembled, object seal 3130 is clamped to a portion of the housing 3102, thus preventing axial (i.e., along longitudinal axis "B-B") movement of the object seal 3130 and further preventing circumferential and radial movement of the object seal 3130.

In use, the obturator member 2014 of the trocar assembly 2010 is introduced within the cannula assembly 3100, through the aperture 3139 of the object seal 3130 and through the zero-closure seal 3150. The assembled unit is positioned against the targeted tissue, e.g., the abdominal lining. When the obturator member 2014 passes through the aperture 3139 (either when longitudinal axis "A-A" is substantially aligned with longitudinal axis "B-B" or when longitudinal axis "A-A" is non-aligned (i.e. spaced from and/or angled) with longitudinal axis "B-B"), the only portion of the object seal 3130 that is capable of circumferential, axial or radial movement is the horizontal surface 3138 adjacent aperture 3139 and disposed within vertical surface 3136a of annular wall 3136. The other portions of the object seal 3130 (including the rigid plastic insert 3130a and the portions of the elastomeric septum seal 3130b disposed outwardly of rigid plastic insert 3130a) are not capable of moving axially or radially with respect to the aperture 3139.

The penetrating head 2020 is manipulated relative to the tissue whereby the cylindrical element 2022, the tapered surfaces 2030, 2032, the dissecting fins 2024 and the central section 2034 engage tissue and dissect or separate the tissue to gain access to an underlying cavity. The obturator member 2014 may then be removed from the cannula assembly 3100. Instruments may be introduced within the cannula assembly 3100 to perform a surgical procedure.

With particular reference to FIGS. 32-39, a trocar assembly 4010 (e.g., a 5 mm version) is shown. Trocar assembly 4010 includes an elongated obturator member 4214 (FIGS. 35-37) and a protective shield 4216 (FIGS. 38-39) coaxially mounted about the obturator member 4214. Trocar assembly 4010 is similar to trocar assembly 2010, discussed above, however the object seal 4330 (FIGS. 33-34) of trocar assembly 4010 is different from the object seal 3130 of trocar assembly 2010 and will be described herein.

The object seal 4330 includes an elastomeric septum seal 4330b which is over-molded onto a rigid plastic insert 4330a. Rigid plastic insert 4330a includes a horizontal surface 4332, and a vertical, annular wall 4334. An inner vertical surface 4334a of annular wall 4334 defines diameter D5. The elastomeric septum seal 4330b of the object seal 4330 defines a horizontal surface 4338 disposed within annular wall 4334. The elastomeric septum seal 4330b includes an aperture 4339 having a diameter D6. The diameter D1 of the cover's aperture 3120 is less than the diameter D5 of the annular wall 4334. Thus, upon insertion, the obturator member 2014 is only able to contact the horizontal surface 4338 and the walls defining the aperture 4339 of the object seal 4330.

The object seal 4330 also includes a lip 4340 depending downwardly from its horizontal surface 4332. The lip 4340 engages a corresponding detent (not shown) on the housing, such that the object seal 4330 cannot move circumferentially (i.e., about longitudinal axis "B-B") or radially (i.e., transversely with respect to longitudinal axis "B-B"). Additionally, when the cannula assembly 3100 is assembled, object seal 4330 is clamped to a portion of the housing 3102, thus preventing axial (i.e., along longitudinal axis "B-B") movement of the object seal 4330 and further preventing circumferential and radial movement of the object seal 4330.

The obturator member 4214 includes an obturator rod 4218 and a penetrating head 4220 at the end of the obturator rod 4218. The penetrating head 4220 includes, from distal to proximal, a cylindrical element 4222 and a dissecting element contiguously extending from the cylindrical element 4222. The cylindrical element 4222 defines a rounded leading surface which is atraumatic to tissue. The cylindrical element 4222 permits initial insertion within an opening in the tissue and facilitates the advancement of the penetrating head 4220 within the tissue without any cutting or incising of the tissue.

The dissecting element incorporates upper and lower planar surfaces and rounded side surfaces which interconnect the planar surfaces, to thereby define a pair of outwardly disposed dissecting fins 4224. The dissecting fins 4224 also are atraumatic to tissue. The dissecting fins 4224 further enlarge the opening within the tissue as the penetrating head 4220 is advanced.

The protective shield 4216 is adapted for reciprocal longitudinal movement relative to the obturator member 4214 between an advanced position and a retracted position. The protective shield 4216 includes a sleeve having a shield head 4226 which is mounted about the penetrating head 4220 of the obturator member 4214. The protective shield 4216 is normally biased toward the advanced position by a coil spring mounted within the obturator housing 4212 and engageable with the sleeve. In the initial or advanced position of the protective shield 4216, the penetrating head 4220 is partially exposed from the shield head 4226. In the retracted position of the protective shield 4216, the cylindrical element 4222 and the dissecting fins 4224 are further exposed from the shield head 4226.

In use, trocar assembly 4010 is introduced through the cannula assembly 3100 and the assembled unit is positioned against the targeted tissue, e.g., the abdominal lining. That is, when the obturator member 4214 passes through the aperture 4339 (either when longitudinal axis "A-A" is substantially aligned with longitudinal axis "B-B" or when longitudinal axis "A-A" is non-aligned (i.e. spaced from and/or angled) with longitudinal axis "B-B"), the only portion of the object seal 4330 that is capable of circumferential, axial or radial movement is the horizontal surface 4338 adjacent aperture 4339. The other portions of the object seal 4330 (including rigid plastic insert 4330a and the portions of the elastomeric septum seal 4330b disposed outwardly of rigid plastic insert 4330a) are not capable of moving axially or radially with respect to the aperture 4339.

Once adjacent the targeted tissue, the penetrating head 4220 is manipulated to engage tissue and initiate the dissecting action on the tissue. The penetrating head 4220 is advanced causing the shield head 4226 to contact the tissue and be driven proximally toward the retracted position. In this position, the dissecting fins 4224 are further exposed to further dissect the tissue. After access to the underlying cavity has been achieved, the protective shield 4216 and the shield head 4226 are returned to the advanced position by the biasing force of the coil spring. The obturator member 4214 may then be removed from the cannula assembly 3100. Instruments may be introduced within the cannula assembly 3100 to perform a surgical procedure.

The materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A surgical system for penetrating tissue, which comprises:
   a cannula assembly including:
      a cannula housing;
      a cannula sleeve depending from the cannula housing and defining a longitudinal axis; and
      an object seal disposed in mechanical cooperation with the cannula housing and being adapted to establish a substantial seal about an object inserted therethrough, the object seal comprising:
         a rigid insert including a first horizontal surface, a first vertical wall disposed inwardly of the first horizontal surface, and a second vertical wall disposed inwardly of the first vertical wall, the first vertical wall having a first diameter, the second vertical wall having a second diameter, the first diameter being larger than the second diameter; and an elastomeric seal disposed in mechanical cooperation with the rigid insert, the elastomeric seal including a horizontal surface disposed within the second vertical annular wall, and the elastomeric seal including an aperture disposed therein for accommodating insertion of a surgical instrument therethrough, the aperture defining a third diameter, the third diameter being smaller than the second diameter;
   an obturator assembly at least partially positionable within the cannula assembly, the obturator assembly including an obturator housing and an obturator member extending from the obturator housing, the obturator member having a leading penetrating member adapted to penetrate tissue.

2. The surgical system of claim 1, wherein the obturator assembly includes an obturator sleeve, the obturator sleeve dimensioned to at least partially accommodate the obturator member.

3. The surgical system of claim 2, wherein the obturator sleeve is adapted for longitudinal movement from an advanced position to a retracted position relative to the obturator member.

4. The surgical system of claim 1, wherein the elastomeric seal is over-molded onto the rigid insert.

5. The surgical system of claim 1, wherein the rigid insert is made of plastic.

6. The surgical system of claim 1, wherein the rigid insert includes a distally-depending lip, the lip being configured to engage a portion of a cannula housing.

7. The surgical system of claim 1, further including a zero closure valve disposed in mechanical cooperation with the cannula housing, the zero closure valve configured to open to permit passage of a surgical object and thereafter close in the absence of the surgical object.

8. The surgical system of claim 1, wherein the cannula housing includes a cover defining a cover aperture that extends through the cover, the cover adapted to enclose the object seal.

9. The surgical system of claim 8, wherein the cover has a trailing end face that defines a predetermined geometrical configuration and the obturator housing has a predetermined geometrical configuration corresponding to the predetermined geometrical configuration of the trailing end face of the cover to enable the obturator housing to mate with the cover.

10. The surgical system of claim 9, wherein the obturator housing includes a leading end that projects outwardly from the obturator housing.

11. The surgical system of claim 10, wherein the leading end of the obturator housing is tapered.

12. The surgical system of claim 8, wherein at least a portion of the trailing end face of the cover is obliquely arranged relative to the longitudinal axis.

13. The surgical system of claim 8, wherein the trailing end face of the cover defines a mounting recess.

14. The surgical system of claim 11, wherein the mounting recess is diamond shaped.

15. The surgical system of claim 8, wherein the cover includes an outer segment and an inner segment depending radially inwardly from the outer segment.

16. The surgical system of claim 15, wherein the inner segment has a planar surface obliquely arranged with respect to the longitudinal axis, the inner segment tapering toward the cover aperture.

17. The surgical system of claim 8, wherein the cover includes at least one peripheral rib adapted to engage the cannula housing.

\* \* \* \* \*